(12) United States Patent
Sherry et al.

(10) Patent No.: US 6,746,662 B1
(45) Date of Patent: Jun. 8, 2004

(54) PH SENSITIVE MRI CONTRAST AGENTS (75) Inventors: A. Dean Sherry, Dallas, TX (US); Shanrong Zhang, Dallas, TX (US); Kuangcong Wu, Richardson, TX (US)

(73) Assignee: Board of Regents the University of Texas System, Austin, TX (US)

( * ) Notice: Subject to any disclaimer, the term of this patent is extended or adjusted under 35 U.S.C. 154(b) by 0 days.

(21) Appl. No.: 09/913,092

(22) PCT Filed: Feb. 9, 2000

(86) PCT No.: PCT/US00/03283

§ 371 (c)(1),
(2), (4) Date: Jan. 9, 2002

(87) PCT Pub. No.: WO00/47111

PCT Pub. Date: Aug. 17, 2000

Related U.S. Application Data (60) Provisional application No. 60/119,348, filed on Feb. 9, 1999.

(51) Int. Cl.[7] .......................... A61K 5/055; C07D 255/02
(52) U.S. Cl. ..................................... 424/9.393; 540/474
(58) Field of Search ................................ 424/1.65, 1.77, 424/9.36, 9.361, 9.363, 9.365, 9.364; 540/465, 474

(56) References Cited

U.S. PATENT DOCUMENTS 5,236,695 A * 8/1993 Winchell et al. ......... 424/9.363
5,573,752 A * 11/1996 Ranganathan et al. ... 424/9.363

* cited by examiner

*Primary Examiner*—Michael G. Hartley (57) ABSTRACT

A composition and method is disclosed for providing a magnetic resonance imaging contrast agent that is sensitive to pH, the compound and salts thereof including, a tetraaza base having a spacer at each of the amide groups, and a proton exchange attached to each of the spacer molecules, wherein the proton exchange group groups mediate proton exchange with water molecules that are trapped within the tetraaza base molecule.

20 Claims, 8 Drawing Sheets

Figure 6 where n=0, 1, 2, 3...

PH SENSITIVE MRI CONTRAST AGENTS

CROSS-REFERENCE TO PROVISIONAL APPLICATION

This application claims the benefit of U.S. Provisional Application No. 60/119,348 entitled, "pH Sensitive MRI Contrast Agents," to A. Dean Sherry et al., filed on Feb. 9, 1999, which is commonly assigned with the present invention and incorporated herein by reference as if reproduced herein in its entirety.

FIELD OF THE INVENTION

The present invention relates in general to the development, characterization and use of contrast agents used for the magnetic resonance imaging of tissue, and more particularly, to the synthesis and use of contrast agents for use during magnetic resonance imaging of samples.

BACKGROUND OF THE INVENTION

Without limiting the scope of the invention, its background is described in connection with magnetic resonance imaging-based systems, as an example.

Heretofore, in this field, gadolinium complexes have been observed to enhance relaxation of water protons via rapid exchange of inner-sphere water molecules with bulk solvent. Recent kinetic results, however, have shown that the lifetime of an inner-sphere water molecule in $Gd^{3+}$ complexes can range from 0.84 ns for aqueous $Gd^{3+}$, 208 ns for $GdDOTA^-$, to over 19000 ns in the tetraamide analog below.

Present gadolinium-based complexes, however, fail to provide customizable solutions to show a contrast where there is no variation in the cellular uptake of the complex. Also, presently available gadolinium-based contrast agents generally provide only an on or off signal, that is, they either cause or fail to cause a contrast. Therefore, presently available compounds are insensitive to particular biological situations and functions.

SUMMARY OF THE INVENTION

It has been found, however, that the present magnetic resonance imaging agents and methods are insensitive to changes in the environment of use. A significant problem of current systems for causing contrast during magnetic resonance imaging is that the user is completely dependent on the differential uptake of the contrast agent by the target around the region to be analyzed. It has been found that certain contrast agents are preferred due to increased uptake of the contrast agent by the target, e.g., tumors. These contrast agents work well as long as the tumor's uptake is greater than that of the surrounding tissue. But if the uptake between the target and the surrounding tissue is similar then no contrast is observed.

Another problem with presently available contrast agents is that, the contrast agent captured by the target provides a single image of the target without regard to its metabolic condition. A contrast agent is required that can be taken up by the target, but that is also able to report on the changing metabolic status of the target vis-a-vis the surrounding tissue.

The present inventors have developed and characterized a new contrast agent for use with magnetic resonance imaging systems that has an unusual pH dependence. One such agent has increased contrast versus the surrounding medium at between pH 4 and 6, reaching a maximum near pH 6, gradually decreasing to a minimum near pH 8.5, then remaining pH insensitive to 10.5. Further characterization of the pH sensitivity and the mechanism by which this occurs was also determined, and was used to develop new agents having varying pH dependence.

More particularly, the present invention is a composition and method for making and using the same as a contrast agent during magnetic resonance imaging (MRI). A compound of the invention has the formula:

wherein R, R', R" and R'" are made up of spacer groups and proton exchange groups such that —R=—spacer group)(proton exchange group). The proton exchange groups of R and R'" are usually the same and are functional groups containing at least one hydrogen that is capable of hydrogen bonding with water. Likewise, the proton exchange groups for R' and R" are usually the same and are functional groups containing at least one hydrogen that is capable of hydrogen bonding with water, although if R and R'" contain functional groups with hydrogens capable of hydrogen bonding with water, some applications may require that R' and R" not have any hydrogens capable of hydrogen bonding. In one embodiment R=R'=R"=R'".

More particularly, the chelating compound may have a inner-sphere water molecule lifetime of greater than 1000 ns. For use as a contrast agent in MRI the chelating compound will be used to chelate lanthanide (III) ions, preferably gadolinium ions. The water relaxivity of the compound, and particularly the proton exchange rate, is dependent upon the pH of the solution. The proton exchange group will generally have a $pK_a$ of less than 10. The spacer group may be, for example, an acetamide moiety.

The present invention is also directed to a magnetic resonance imaging contrast agent that includes a gadolinium ion and a tetraamide base complexed to the gadolinium ion having the formula:

wherein the tetraamide base comprises four proton-exchange groups attached to each nitrogen atom of the tetraamide base, and wherein the proton-exchange groups are selected from the group consisting of phosphonates, sulfonates, carboxylates, imidazoles or acidic alcohols.

Finally, a method of increasing the contrast of magnetic resonance images of a patient is disclosed that includes;

administering to a patient in need of magnetic resonance imaging a diagnostically effective amount of a tetraamide compound or a salt thereof having the formula:

wherein R, R', R" and R'" have a spacer group and a proton exchange group, wherein the proton exchange groups for R and R'" are functional groups containing a hydrogen capable of hydrogen bonding with water, and the proton exchange groups for R' and R" are the same and are functional groups containing a hydrogen capable of hydrogen bonding with water.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE PREFERRED EMBODIMENT

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

Figure 1:
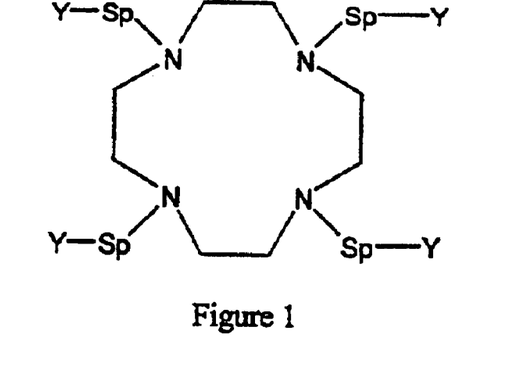
FIG. 1 is a tetraaza-based cyclododecane non-coordinated lanthanide chelator base molecule.

FIG. 1 is a tetraaza-based cyclododecane non-coordinated chelator base molecule of the present invention. The molecule 1,4,7,10-tetraazacyclododecane has substituents attached to each of the macrocycle nitrogens. Each substituent contains a spacer group (Sp) that is attached to the macrocycle nitrogen and a proton exchange group (Y) that is attached to the spacer group. One example showing a spacer group and a proton exchange group, is as follows: The protons on the proton exchange groups (Y) readily exchange with the protons of water molecules that are sequestered by the lanthanide complexed chelators.

Spacer Group  Proton Exchange Group

When a lanthanide ion, one preferred example being a gadolinium atom, is within the cage formed by the tetraaza-based cyclododecane and the spacer groups, the exchange rate of protons between a sequestered water molecule and the proton exchange groups varies with the pH of the solution. This variation in the proton exchange rate is proportional to the relaxation rate of the protons in the bulk solution. Thus the magnetic resonance relaxivity of the protons in the vicinity of the contrast agent varies according to the pH of the region. The proton exchange groups (Y) may be the same or different as described herein below, thereby shifting the pH range of sensitivity.

Figure 2:
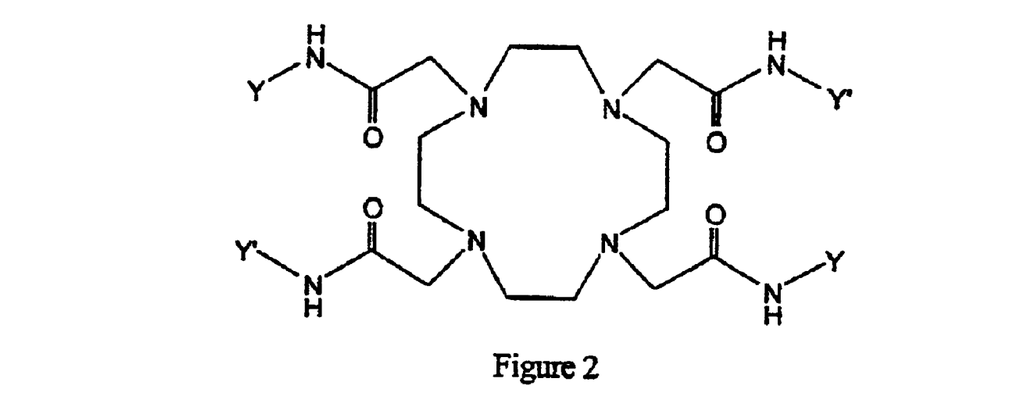
FIG. 2 is one example of a tetraaza-based cyclododecane non-coordinated chelator base wherein the extender group is a acetamide group.

FIG. 2 is one example of a tetraaza-based cyclododecane non-coordinated chelator base in which an acetamide spacer group has been attached to each of the macrocycle nitrogens. The acetamide spacer groups forms a cage-like structure with the tetraaza cyclododecane to trap a metal ion, such as gadolinium. When chelating gadolinium with the acetamide spacer containing tetraaza cyclododecane, proton exchange groups having protons capable of hydrogen bonding to water (usually having a $pK_a$ of less than 10) can exchange with protons on the sequestered water molecules within the molecular cage. In fact, an important part of this invention is the fact that water molecules complexed with the gadolinium do not readily exchange with water molecules of the bulk solvent as is the case with other MRI contrast agents. The lifetime of an inner-sphere water molecule should be over 1000 ns, preferably over 10,000 ns.

Figure 3:
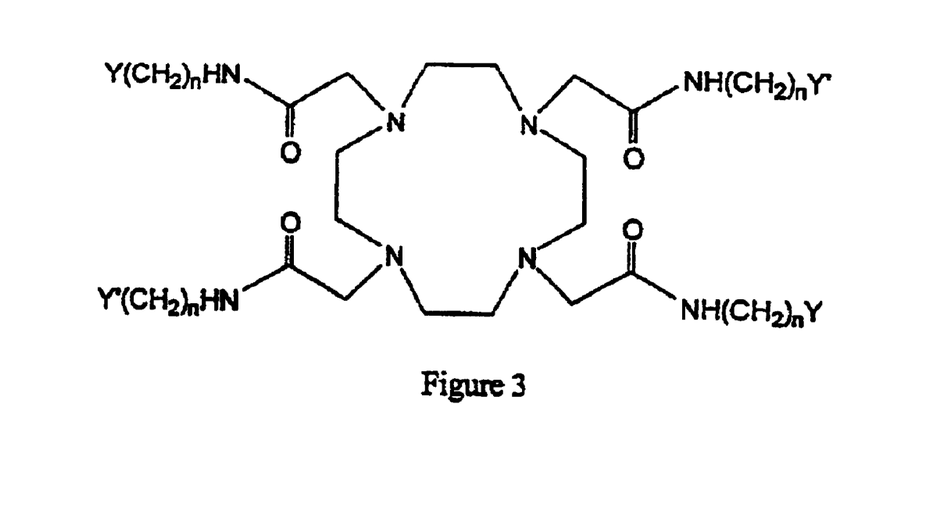
FIG. 3 is another example of a tetraaza-based cyclododecane non-coordinated chelator base wherein the extender group is an N-alkyl acetamide group.

FIG. 3 is another example of a tetraaza-based cyclododecane non-coordinated chelator base having a acetamide based spacer, but in this case having an additional alkyl spacer, containing between 1 and 5 carbon atoms, between the acetamide nitrogen and the proton exchange group (Y).

The spacer group (Sp) as shown in FIG. 1 can be one of a number of possible substituents. The function of the spacer is to help provide an environment that will increase the lifetime of an inner-sphere water molecule to a time long enough so that the lifetime is longer than the proton exchange rate between the proton exchange groups and the inner-sphere water molecule. One example of such a group is the acetamide group. The acetamide group functions to increase the lifetime of an inner-sphere water molecule to a useful time. Other organic functional groups with similar electronegative properties would be natural equivalents to acetamide. Additionally, acetamide analogs may be used wherein one of the methylene hydrogens of the acetamide group is replaced with a some organic substituent. Accordingly, any organic functional group that may be placed between the macrocycle nitrogens and the proton exchange groups of FIG. 1 that increase the lifetime of an inner-sphere water molecule to greater than 1000 ns, or preferably 10,000 ns, are considered to be part of this invention.

The proton exchange groups that are responsible for proton exchange with a sequestered water molecule may be any functional groups that contain hydrogens capable of hydrogen bonding with water. Sonic examples of such groups are, but are not limited to, phosphonates, sulfonates, carboxylates, imidazoles and alcohols, such as phenol or other relatively acidic alcohols. Generally, the proton exchange groups will have a p$K_a$ of less than 10, thereby providing protons that can readily exchange with water. To decrease the pH sensitivity range of the chelating, or MRI contrast agent, two or four sulfonate groups may serve as Y groups. Likewise, it is expected that the use of carboxyl groups will have a like effect. To shift the pH range toward higher or mixed pH sensitivity ranges, imidazoles, phosphonates or phenolic groups may be used. Combinations of pairs of the proton exchange groups are expected to provide refined pH sensitivity ranges that are caused by the combination. These combinations of pairs may be synthesized as generally disclosed herein below.

Figure 4:
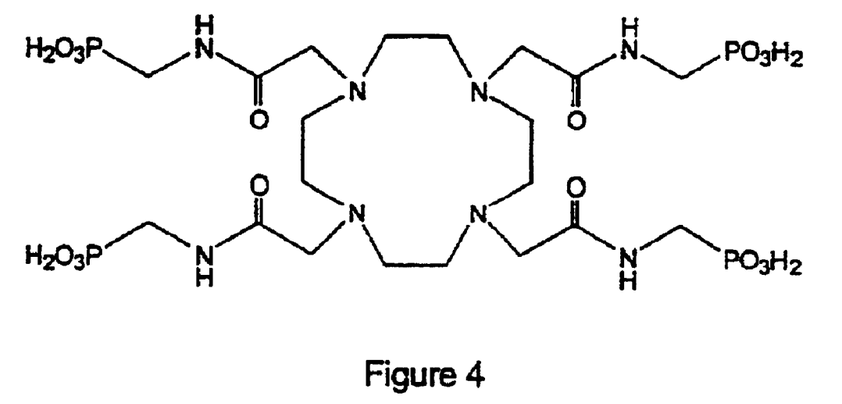
FIG. 4 is another example of a tetraaza-based cyclododecane non-coordinated chelator base wherein the extender group is an acetamide group and the proton exchange groups are all the same and are phosphonate groups.

FIG. 4 is a pH dependent contrast agent in which a non-coordinated tetraaza compound having extended phosphonate groups attached to an acetamide spacer. The present inventors began by synthesizing and characterizing one of the new derivatives disclosed herein and observed that the water proton relaxivity of the compound in FIG. 4 had an unusual pH dependence, increasing between pH 4 and 6, reaching a maximum near pH 6, gradually decreasing to a minimum near pH 8.5, then remaining pH insensitive to 10.5.

Figure 5:
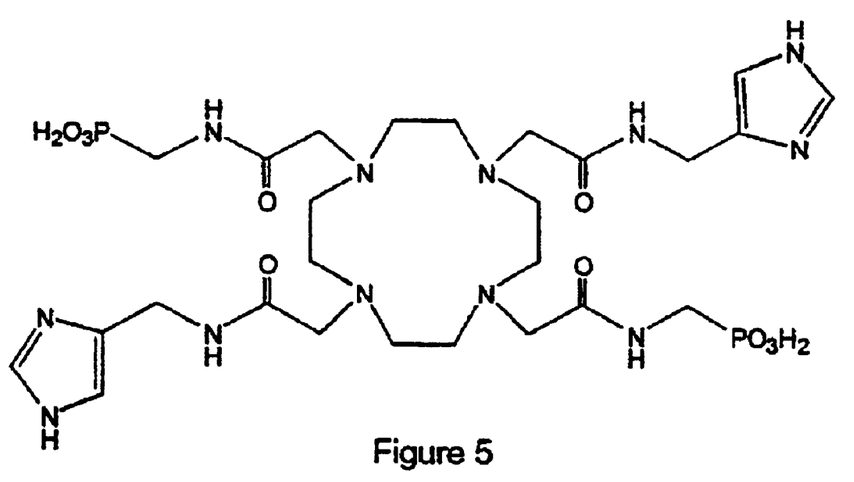
FIG. 5 is another example of a tetraaza-based cyclododecane non-coordinated chelator base wherein the extender group is an acetamide group and the proton exchange groups are mixed and are imidizole and phosphonate groups.
Figure 6:
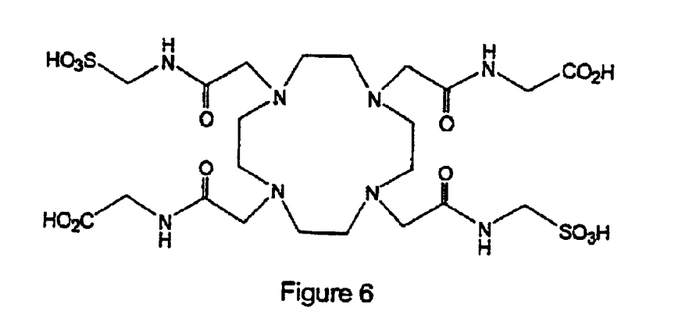
FIG. 6 is another example of a tetraaza-based cyclododecane non-coordinated chelator base wherein the extender group is an acetamide group and the proton exchange groups are mixed and are sulfonate and carboxylate groups.
Figure 7:
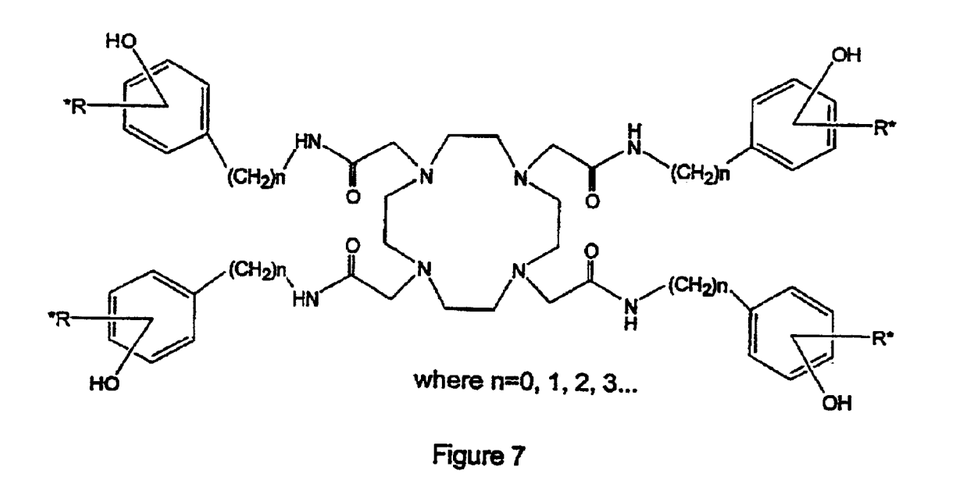
FIG. 7 is another example of a tetraaza-based cyclododecane non-coordinated chelator base wherein the extender group is an acetamide group and the proton exchange groups are either mixed or the same and are substituted or non-substituted phenols.

FIG. 5 is yet another embodiment of a pH sensitive contrast agent of the present invention in which the proton exchange groups across from each other, that is, at opposite ends of the tetraaza-based cyclododecane are the same, whereas adjacent substituents are not. In this example, a pair of imidizole groups and a pair of phosphonate groups are located opposite from each other. FIG. 6 shows an embodiment wherein a pair of carboxyl groups and a pair of sulfonate groups are located on opposite ends of the base molecule. While in FIG. 7, a pair of substituted phenol groups are located opposite from each other, and wherein the same or a different pair may be positioned at opposite ends of the tetraaza base.

The water relaxivity of other gadoliniuim based contrast agents has been shown to be independent of pH between 2 and 8, but increases at both low and high pH due to H$^+$ and OH$^-$ catalyzed prototropic exchange of the bound water protons. Given that water exchange for the compound depicted in FIG. 4 is also slow over the entire pH range, the present inventors fit the relaxivity curve to standard Solomon-Bloembergen theory, $R_{1P}=(N/55.5)q(T_{1M}+\tau_M)^{-1}+R_{1p}^{OS}$, where N is the molar concentration of the complex, q is the number of inner-sphere coordinated water molecules, $T_{1M}$ is the longitudinal relaxation time of the coordinated water protons and $R_{1p}^{OS}$ is the outer-sphere relaxation rate.

It was found that as the increases in relaxivity of the contrast agent in FIG. 4 above pH 10.5 are similar to those reported other gadolinium based contrast agents, the present inventors assumed that $\tau_M$ is dominated by prototropic exchange rather than bulk water molecule exchange, and proportional to $1/(k_1+k_2*[OH^-])$ in basic environments. By assuming that $k_1$ ($1/\tau_M=5.26\times10^4$ s$^{-1}$, from $^{17}$O NMR) is constant above pH 8.5, a fit of the high pH relaxivity data (pH>9.5) gave $k_2=8.09\times10^7$ M$^{-1}$s$^{-1}$, a value that is significantly smaller $k_2=1.4\times10^{10}$ M$^{-1}$s$^{-1}$) than that reported for other gadolinium-based contrast agents.

Figure 8:
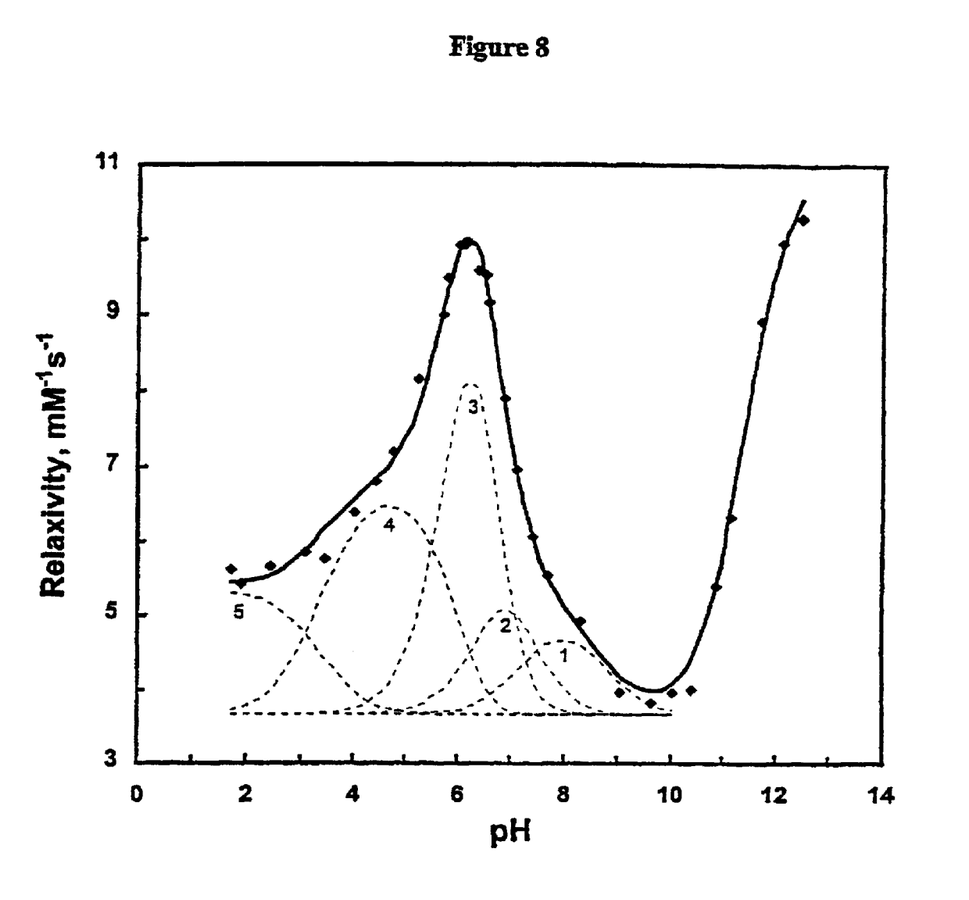
FIG. 8 is a graph plotting the relaxivity of a contrast agent of the present invention verses the pH of the solution.

Potentiometric titration of the complex between the molecule in FIG. 4 and a gadoliniun ion-hereinafter "Gd(1)" (combinations with other lanthanides are designated Ce(1), Dy(1), etc.)—revealed protonation steps between pH 9 and 2 (log $K_n$=8.70, 7.28, 6.55, 6.02, and 3.38) that were similar to those found for free ligand (log $K_n$=7.93, 7.30, 6.64, 6.11, and 2.39). These likely reflect protonation of the uncoordinated phosphonate groups. The first four protonation constants were similar to those for LnDOTP$^{5-}$ complexes (Ln$^{3+}$=Ce$^{3+}$, Nd$^{3+}$, Gd$^{3+}$, Tm$^{3+}$ and Lu$^{3+}$), consistent with p$K_2$ values for each of the uncoordinated phosphonates. The shape of the pH dependent relaxivity curve over this range indicates that each protonated species has a unique water proton relaxivity. A fit of these data to a model involving five protonated species (the protonation constants were fixed to those determined by potentiometry) gave $R_1$ values of 5.3, 6.7, 13.3, 6.3, 5.1 and 3.7 mM$^{-1}$s$^{-1}$ for Gd(1)H$_5$, Gd(1)H$_4$, Gd(1)H$_3$, Gd(1)H$_2$, Gd(1)H$_1$ and Gd(1), respectively. Interestingly, the calculated relaxivity of Gd(1)H$_3$ is notably higher than the other species, and indeed this species provides the main contribution to the maximum in the relaxivity curve near pH 6. The dashed curves under the solid relaxivity curve in FIG. 8 shows the population of each protonated species and its contribution to the bulk $R_1$ as a function of pH.

Ion-pairing interactions, between a compound having the structure shown in FIG. 2 where Y=Y'=CH$_3$ and the anions triflate or phosphate, are stabilized by a hydrogen-bonding network created by the slowly exchanging water molecule and the four amide protons. Disruption of this H-bonding network by protonation of the anion releases the anion, thereby allowing prototropic exchange between the coordinated water and bulk solvent. For the compounds represented in FIG. 2, where Y and/or Y' are proton exchange groups, ion-pairing interactions are replaced by the covalently attached phosphonates so even as low as pH 2 where these groups are not fully protonated, this H-bonding network is not completely destroyed. Thus, prototropic exchange of the bound water protons at low pH appears to be inhibited by the strong H-bonded network created by the phosphonates, the amides, and the single coordinated water molecule. The present inventors observed that prototropic exchange of water protons is maximized in the triprotonated species indicates that three phosphonate groups may be dynamically involved in the H-bonding network involving the bound water molecule and that H$^+$ exchange with bulk water is maximized when those phosphonates are monoprotonated. At pH values above 8 where all of the phosphonate protons are removed, the proton exchange network is destroyed and the relaxivity of Gd(1) (FIG. 8) decreases to that of an outer-sphere complex.

The unusual pH dependency of the bulk water relaxivity of Gd(1) makes it a potentially useful pH sensitive MRI contrast agent. To demonstrate this. typical $T_1$ weighted proton images of a phantom consisting of four 5 mm tubes containing either 0.2 mM GdDTPA$^{2-}$ or Gd(1), at ph 6 and 9, were recorded using a 4.7 T imaging system data not shown. The cross-sectional images of the tubes illustrate that the intensities of the two GdDTPA$^{2-}$ samples are identical at the two pH values, while the intensities of the Gd(1) samples differ considerably. The intensity of the Gd(1) sample at pH 6 was higher than either sample of GdDTPA$^{2-}$, consistent with its higher relaxivity at this pH. Conversely, the Gd(1) sample at pH 9 was the least intense, consistent with an outer-sphere relaxation mechanism. Although other approaches to preparing gadolinium complexes with relaxivities that are sensitive to pH over the physiological range have been proposed, the present results demonstrate that it is possible to modulate prototropic exchange by the extended pendant arms in ligands such as depicted in FIG. 4, to design a series of pH sensitive contrast agents with differing tissue distributions and pH sensitivities.

To provide further insight into the mechanism of this most interesting relaxation behavior, the present inventors next examined the solution structure of various Ln(1) complexes by NMR. The $^{31}$P NMR spectra of various Ln(1) complexes (except Gd$^{3+}$) showed single resonances with chemical shifts not dramatically different from that of the free ligand. In comparison with the highly shifted $^{31}$P resonances in the analogous LnDOTP$^{5-}$ complexes, this result indicated that the four phosphonate groups of Ln(1) are situated relatively far from the paramagnetic center, likely not coordinated to the central ion. The $^1$H and $^{13}$C NMR spectra of Ln(1) were all consistent with single molecular species having high stereochemical rigidity. Next, the inventors found that the hyperfine shifts of the macrocyclic protons of Yb(1) mirrored those of YbDOTP$^{5-}$, YbDOTA$^+$, and YbDOTMA$^-$. These results indicated that the Yb$^{3+}$ is chelated by the four amide oxygens and four macrocyclic nitrogens. Measurement of the $^{17}$O NMR chemical shifts of water in the presence of variable amounts of Dy(1) confirmed that a single water molecule is directly coordinated to Dy$^{3+}$, while variable temperature $^{17}$O NMR linewidth measurements revealed a water exchange lifetime ($\tau_M$) of 19±1 μs, at both pH 7.6 and 9.5.

EXAMPLES

Figure 10:
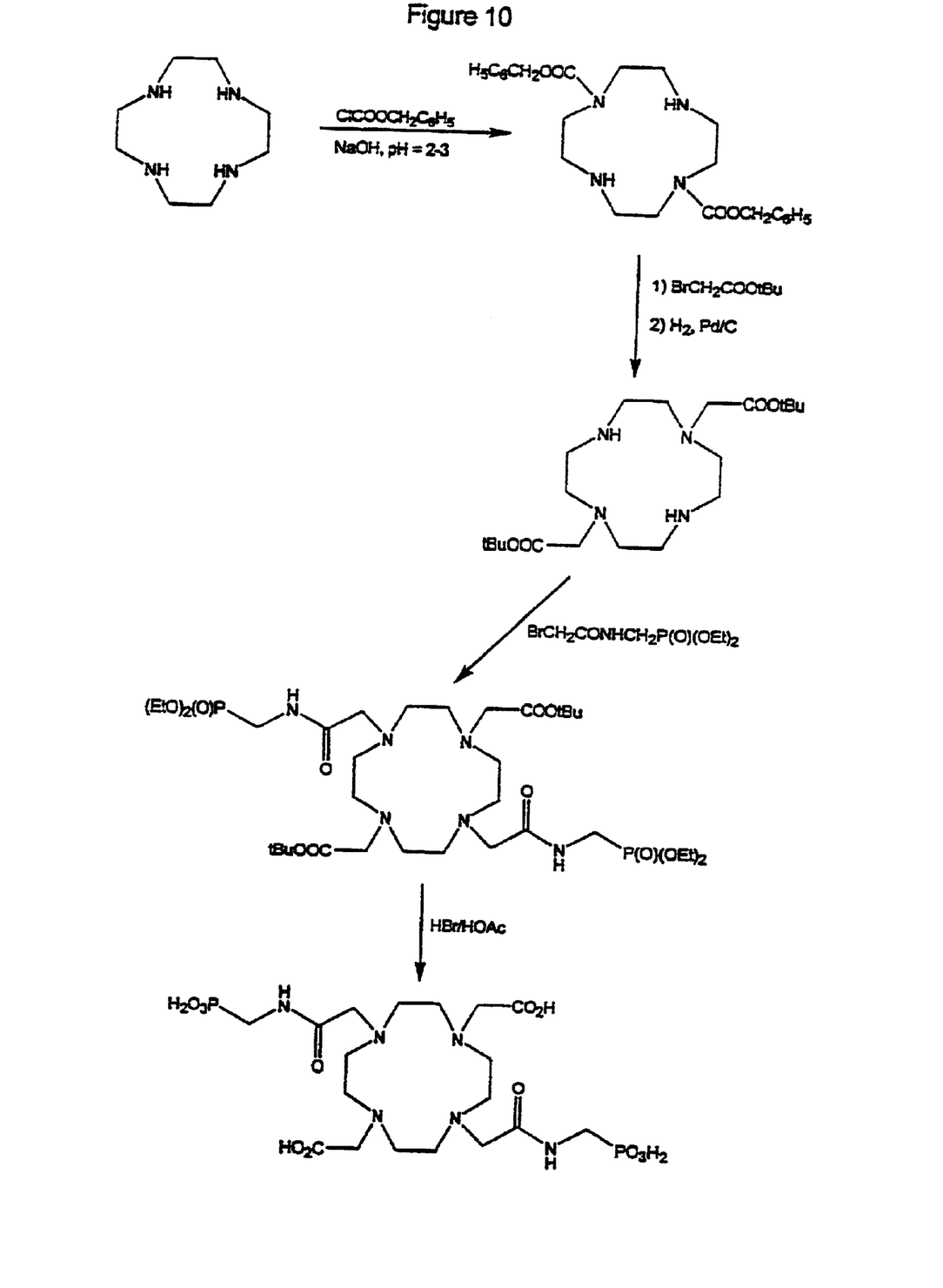
FIG. 10 is a synthetic pathway for forming a molecule wherein (R=R'")≠(R'=R")
Figure 11:
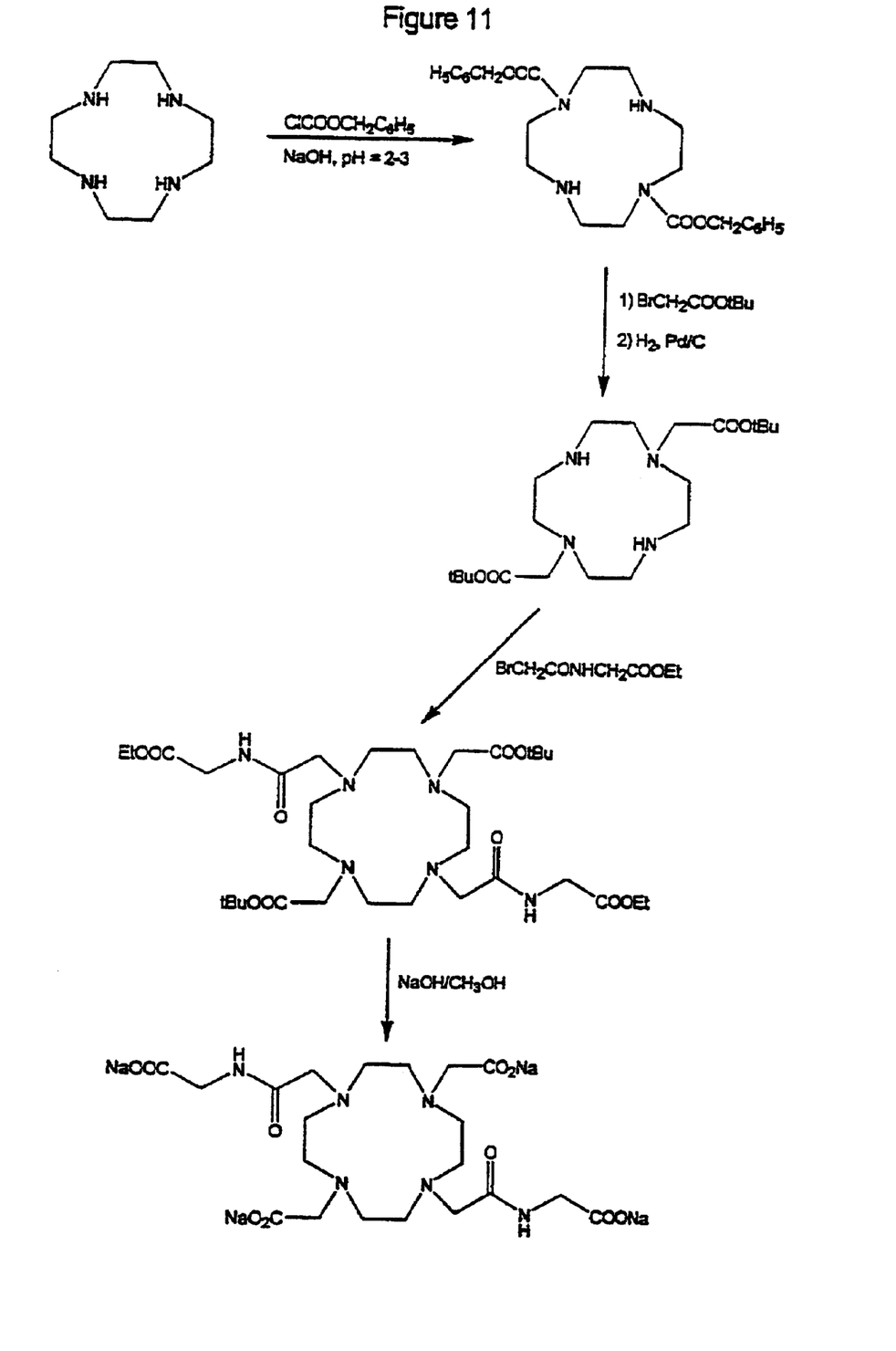
FIG. 11 is another synthetic pathway for forming a molecule wherein (R=R'")≠(R'=R")
Figure 12:
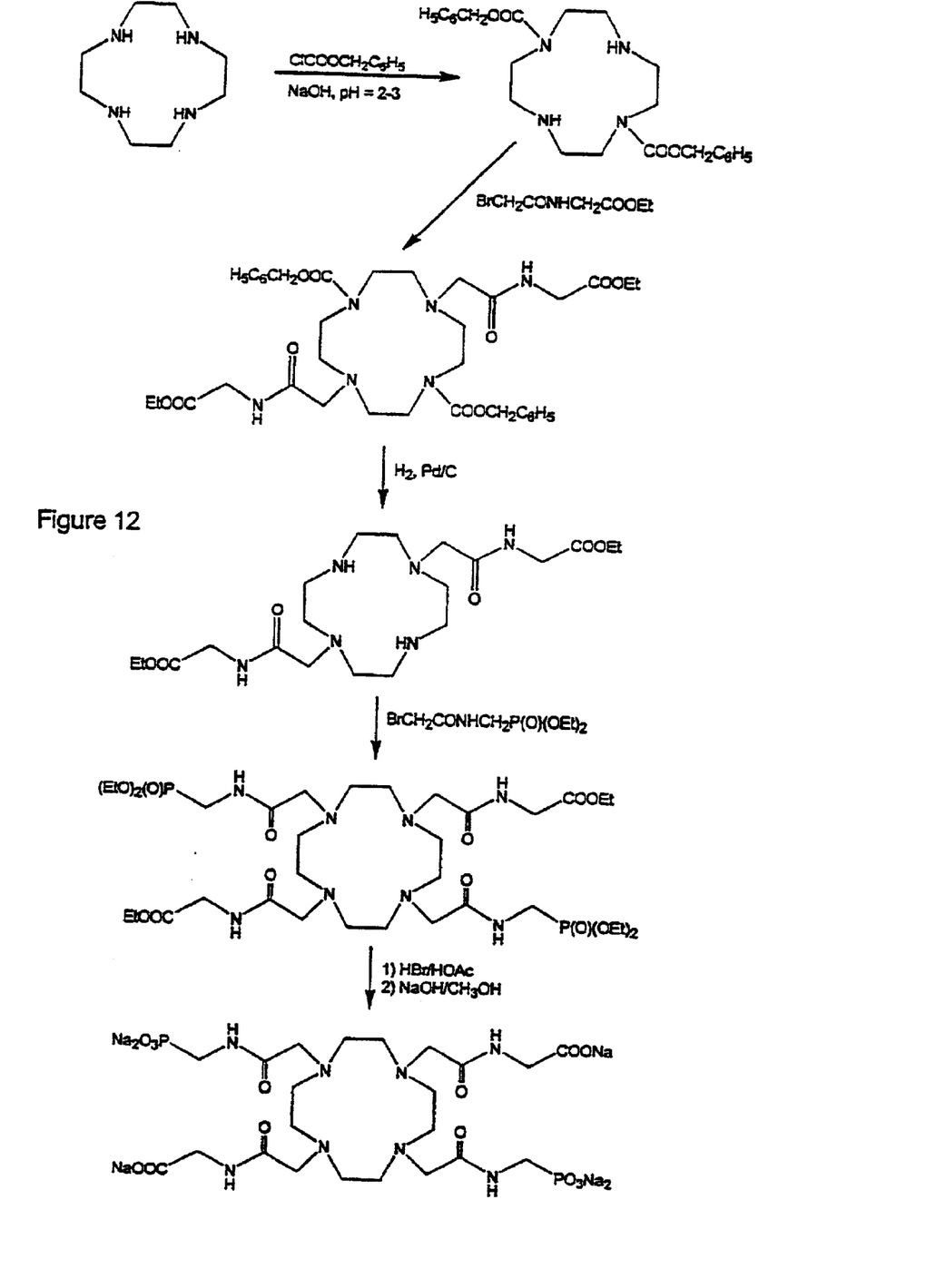
FIG. 12 is another synthetic pathway for forming a molecule wherein (R=R'")≠(R'=R")

The formation of mixed side chain molecules, where (R=R''')≠(R'=R'') has been described in, e.g., U.S. Pat. No. 5,428,155, issued to Sherry; and Kovacs and Sherry, "pH-Controlled Selective Protection of Polyaza Macrocycles," Synthesis, pp 761–763, (July 1997), the relevant portions of which are incorporated herein by reference. Examples of such synthetic pathways are shown if FIGS. 10–12. The synthesis of certain compounds disclosed herein are disclosed in greater detail.

Figure 9:
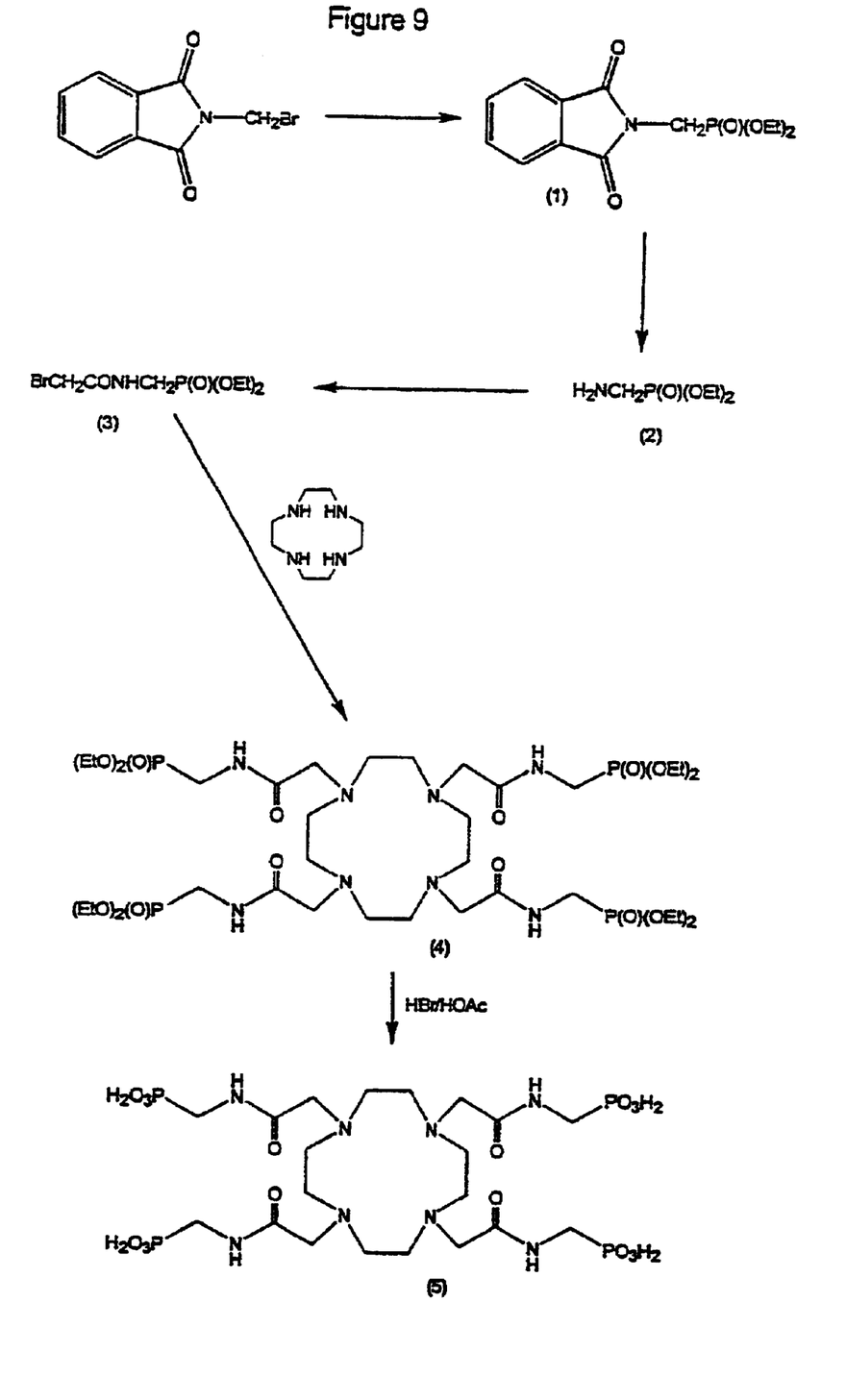
FIG. 9 is a synthetic pathway for forming a molecule wherein R=R'=R"=R'"

Synthesis of 1,4,7,10-tetraazacyclododecane-1,4,7, 10-tetrakis(acetamidomethylphosphonic acid) (FIG. 9) and Formation of Complexes with Lanthanide (III) Ions Diethyl Phthalimidomethylphosphonate (1)

N-(Bromomethyl)-phthalimide (14.4 g, 0.06 mol) and triethyl phosphite (12.0 g, 0.072 mol) were placed in a round-bottomed flask equipped with a reflux condenser and heated at 85–100° C. for 30 min. After the exothermic reaction had subsided, the flask was fitted for simple distillation and ethyl bromide was distilled from the reaction mixture with heating at 100–110° C. for 2 hours. The resulting light yellow oil solidified at room temperature. The crude product was washed with hexane and recrystallized from diethyl ether/hexane to yield white crystals. 16.0 g, 89.9%; mp 66–67° C. (lit. 67° C.); $^1$H NMR (CDCl$_3$) δ 7.76 (m, 4H, C$_6$H$_4$), 4.19 (q, 4H, OCH$_2$), 4.17 (d, 2H, CH$_2$P), 1.33 (t, 6H, CH$_3$).

Diethyl Aminoimethylphosphonate (2)

To a solution of compound 1 (25.0 g, 0.085 mol) in absolute ethanol (300 ml) was added hydrazine (3.2 ml). The mixture was stirred at room temperature overnight and then refluxed for 3 hours. After cooling the sample in a refrigerator, the precipitate formed was collected by suction filtration and washed with benrzene. The solvent was removed from the filtrate and the resulting light yellow oil was purified using a column of silica gel (methanol/diethyl ether, 1:2) to afford a colorless oil. 9.8 g, 68.3%. $^1$H NMR (CDCl$_3$) δ 4.15 (m, 4 H, OCH$_2$), 3.02 (d, 2H, CH$_2$P), 1.67 (br, 2H, H$_2$N), 1.35 (t, 6H, CH$_3$); $^{13}$C NMR (CDCl$_3$) δ 61.58 (d, OCH$_2$), 37.49 (d, CH$_2$P), 16.11 (d, CH$_3$).

Diethyl Bromoacetamidomethylphosphonate (3)

To a mixture of compound 2 (7.0 g, 0.042 mol) and potassium carbonate (7.0 g, 0.051 mol) in benzene (50 ml) was added bromoacetyl bromide (3.7 ml, 0.042 mol) at 0° C. The mixture was stirred at room temperature overnight. The solid was removed by filtration and the solvent was evaporated from the filtrate. The resulting residue was purified using a column of silica gel (10% methanol in diethyl ether) to afford a white solid. 9.6 g, 79.3%. $^1$H NMR (CDCl$_3$) δ 8.08 (br, 1H, NH), 4.16 (m, 4H, OCH$_2$), 3.92 (s, 2H, BrCH$_2$), 3.75 (q, 2H, CH$_2$P), 1.35 (t, 6H, CH$_3$); $^{13}$C NMR (CDCl$_3$) δ 166.38 (d, CO), 62.65 (d, OCH$_2$), 35.00 (d, CH$_2$P), 28.02 (s, BrCH$_2$), 16.16 (d, CH$_3$).

1,4,7,10-tetraazacyclododecane-1,4,7,10-tetrakis(diethyl-acetamidomethylphosphonate) (4)

To a mixture of cyclen (0.43 g, 0.0025 mol) and potassium carbonate (1.5 g, 0.011 mol) in acetonitrile (10 ml) was added compound 3 (2.88 g, 0.01 mol). The mixture was stirred at 60–70° C. for 6 hours. The solid was filtered off and the solvent was removed from the filtrate. The residue was dissolved in chloroform and the resulting solution was refluxed for 30 min with the formation of precipitate. After the solid was filtered off, the solvent was removed from the filtrate to give product as a pale yellow solid, 2.48 g, which was used in the next step without further purification. $^1$H NMR (CDCl$_3$) δ 7.93 (br, 4H, NH), 4.14 (m, 16H, OCH$_2$), 3.73 (br m, 8H, CH$_2$P), 3.20 (br, 8H, CH$_2$CO), 2.77 (br, 16H, NCH$_2$CH$_2$N), 1.33 (t, 24H, CH$_3$); $^{13}$C NMR (CDCl$_3$) δ 170.95 (CO), 62.33 (d, OCH$_2$), 58.97 (CH$_2$CO), 53.67 (NCH$_2$CH$_2$N), 34.25 (d, CH$_2$P), 16.28 (d, CH$_3$).

1,4,7,10-tetraazacyclododecane-1,4,7,10-tetrakis (acetamidomethylphosphonic Acid) (5)

Compound 4 (0.8 g, 0.8 mmol) was dissolved in 30% solution of hydrogen bromide in glacial acetic acid (8 ml). The resultant solution was stirred at room temperature overnight, followed by evaporation of the solvent and excess hydrogen bromide in vacuo. The residue was dissolved in ethanol and the solvent was evaporated to remove any traces of acetic acid. The resulting solid was dissolved in methanol and diethyl ether was added slowly with stirring. The resulting precipitate was separated and dissolved in water. Lyophilization produced a white solid. 0.53 g, 85.5%. $^1$H NMR (D$_2$O) δ 3.72 (br, 8H, CH$_2$CO), 3.52 (d, 8H, CH$_2$P), 3.25 (br, 16H, NCH$_2$CH$_2$N); $^{13}$C NMR (D$_2$O) δ 170.65 (CO), 56.50 (CH$_2$CO), 51.83 (NCH$_2$CH$_2$N), 38.24 (d, CH$_2$P); combustion analysis for C$_{20}$H$_{44}$N$_8$O$_{16}$P$_4$.2.2HBr.4.6H$_2$O:

|  | % C | % H | % N |
|---|---|---|---|
| Calculated | 23.16 | 5.38 | 10.80 |
| Found | 23.06 | 5.66 | 10.84 |

Lanthanide(III) Complexes

Lanthanide(III) solutions were prepared by dissolving the corresponding salts into water to make an approximate concentration of 0.2M. These solutions were standardized by titration with EDTA in pH=5.2 acetate buffer, using xylenol orange as an end point indicator. Compound 5 was dissolved into water to a concentration about 0.05M, and 1 equivalent of lanthanide solution was slowly added. The solution was stirred at room temperature overnight. The pH of solution was adjusted to 9 by the addition of NaOH solution, and then the solution was kept at room temperature overnight. The removal of water yielded the desired complex.

The compounds of the present invention were prepared as described hereinabove, but may also be prepared following different synthetic routes, as will be known to those of skill in the art. While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A chelating compound for use in magnetic resonance imaging, or a salt thereof, comprising:

a tetraaza base having the formula:

wherein pendent arms R, R', R" and R'" each include an acetamide spacer group, at least two of said acetamide spacer groups which terminate with proton exchange groups containing at least one hydrogen atom that is configured to hydrogen bond to an inner-sphere water molecule associated with a trivalent lanthanide ion coordinated to amide oxygens of said acetamide spacer groups and to nitrogen atoms of said tetraaza base such that said inner-sphere water molecule has a average lifetime of greater than 1000 ns.

2. The chelating compound as recited in claim 1 wherein said proton exchange groups have $pK_a$ of less than 10.

3. The chelating compound as recited in claim 1 wherein each of said acetamide spacer groups of said pendent arms R, R', R" and R'" are terminated with said proton exchange group.

4. The chelating compound as recited in claim 3 wherein said proton exchange group comprises first proton exchange groups in said pendent arms R and R'" that are identical and second proton exchange groups in said pendent arms R' and R" that are identical, wherein said first proton exchange groups are different from said second proton exchange groups.

5. The chelating compound as recited in claim 1, wherein each said proton exchange group in said pendent arms R, R', R" and R'" is independently selected from the group consisting of:

phosphonates, sulfonates, carboxylates, imidazoles or alcohols.

6. The chelating compound as recited in claim 3 wherein said proton exchange groups are identical.

7. The chelating compound as recited in claim 1 further comprising said trivalent lanthanide ion and said inner sphere water molecule.

8. The chelating compound as recited in claim 7 wherein said chelating compound is in an aqueous solution and a proton relaxivity of water molecules associated with said chelating compound is dependent upon a pH of said aqueous solution.

9. The chelating compound as recited in claim 8, wherein said proton relaxivity decreases by at least about 0.5 $mM^{-1}s^{-1}$ per pH unit when said pH increases from about 6 to about 8.

10. The chelating compound as recited in claim 7, wherein said inner-sphere water molecule has an exchange rate that is less than a proton exchange rate between said proton exchange groups and said inner-sphere water molecule.

11. The chelating compound as recited in claim 4, wherein said first proton exchange group is an imidizole; and said second proton exchange group is a phosphonate.

12. The chelating compound as recited in claim 6, wherein said proton exchange groups are phenols.

13. The chelating compound as recited in claim 6, wherein said proton exchange groups are phosphonates.

14. A magnetic resonance imaging contrast agent, or a salt thereof, comprising:

a tetraaza base having the formula:

wherein pendent arms R, R', R" and R'" each include an acetamide spacer group at least two of said acetamide spacer groups which terminate with proton exchange groups containing at least one hydrogen atom;

a gadolinium ion that is coordinated to amide oxygens of said acetamide spacer groups and to nitrogen atoms of said tetraaza base; and an inner sphere water molecule that is hydrogen bonded to said proton exchange groups and said inner-sphere water molecule having an average lifetime that varies with a pH of an aqueous solution containing said contrast agent.

15. The magnetic resonance contrast agent as recited in claim 14, wherein a lifetime of said inner-sphere water molecule is greater than 1000 ns.

16. The magnetic resonance contrast agent as recited in claim 14, wherein water molecules associated with said contrast agent have a proton relaxivity that is pH dependent.

17. The magnetic resonance contrast agent as recited in claim 16, wherein said proton relaxivity decreases by least about 0.5 $mM^{-1}s^{-1}$ per pH unit when said pH increases from about 6 to about 8.

18. The magnetic resonance contrast agent as recited in claim 17, wherein said gadolinium ion changes from a triprotonated species to a diprotonated species as said pH increases from about 6 to about 8.

19. A method of using a contrast agent to obtain magnetic resonance images of a patient comprising:

administering to a patient a magnetic resonance imaging contrast agent, or a salt thereof, comprising:

a tetraaza base having the formula:

wherein pendent arms R, R', R" and R'" each include an acetamide spacer group at least two of said acetamide spacer groups which terminate with proton exchange groups containing at least one hydrogen atom;

a gadolinium ion that is coordinated to amide oxygens of said acetamide spacer groups and to nitrogen atoms of said tetraaza base; and an inner sphere water molecule that is hydrogen bonded to said proton exchange groups and said inner-sphere water molecule having an average lifetime that varies with a pH of an aqueous solution containing said contrast agent; and taking a magnetic resonance image of the patient.

20. The method as recited in claim 19, wherein said inner sphere water molecule has a lifetime greater than 1000 ns.

* * * * *